United States Patent
Li et al.

(10) Patent No.: US 12,001,005 B2
(45) Date of Patent: Jun. 4, 2024

(54) OPTICAL ADAPTER FOR MICROSCOPE AND METHOD FOR ADJUSTING DIRECTION OF OPTICAL IMAGE

(71) Applicant: Zumax Medical Co., Ltd., Jiangsu (CN)

(72) Inventors: Jianyue Li, Jiangsu (CN); Xiaoguang Yang, Jiangsu (CN); Lei Du, Jiangsu (CN); Bin Huang, Jiangsu (CN); Quanwu Zhang, Jiangsu (CN)

(73) Assignee: Zumax Medical Co., Ltd., Jiangsu (CN)

( * ) Notice: Subject to any disclaimer, the term of this patent is extended or adjusted under 35 U.S.C. 154(b) by 0 days.

(21) Appl. No.: 18/195,969

(22) Filed: May 11, 2023

(65) Prior Publication Data
US 2023/0280580 A1    Sep. 7, 2023

Related U.S. Application Data

(63) Continuation of application No. 16/496,045, filed on Sep. 20, 2019, now Pat. No. 11,693,224.

(51) Int. Cl.
*G02B 21/36*    (2006.01)
*A61B 3/135*    (2006.01)
(Continued)

(52) U.S. Cl.
CPC .......... *G02B 21/361* (2013.01); *A61B 3/135* (2013.01); *A61B 3/14* (2013.01); *G02B 21/0012* (2013.01)

(58) Field of Classification Search
CPC .. G02B 21/361; G02B 21/0012; G02B 23/16; A61B 3/135; A61B 3/14
(Continued)

(56) References Cited

U.S. PATENT DOCUMENTS 6,072,625 A    6/2000    Kitahara et al.
6,259,563 B1   7/2001    Ecker
(Continued)

FOREIGN PATENT DOCUMENTS

CN    201203701 Y    3/2009
CN    202235302 U    5/2012
(Continued)

OTHER PUBLICATIONS

Examiner provided machine translation of CN 204188876 (Year: 2015).*
(Continued)

*Primary Examiner* — Balram T Parbadia
*Assistant Examiner* — Rahman Abdur
(74) *Attorney, Agent, or Firm* — EcoTech Law Group, P.C.

(57) ABSTRACT

An optical adapter for connecting between a beam splitter of a surgical microscope or an ophthalmic slit lamp microscope and a digital camera equipment including mobile phones, tablet computers, cameras, video cameras with image capturing function is provided. The optical adapter includes a lens group located on an optical path and an optical image rotating lens group for adjusting a direction of an optical image on a photosensitive unit of the digital camera equipment. The optical image rotating lens group is configured to be either independently rotatable around optical axis or be set fixedly. Embodiments of the present invention provide a system and method for real-time adjustment of the direction of an optical image on the photosensitive unit of a digital camera equipment, where regardless of the position of the digital camera a satisfactory direction of the optical image can be obtained with a simple user friendly and convenient structure.

14 Claims, 8 Drawing Sheets

(51) Int. Cl.
*A61B 3/14* (2006.01)
*G02B 21/00* (2006.01)

(58) Field of Classification Search
USPC ........................................................ 359/363
See application file for complete search history.

(56) References Cited

U.S. PATENT DOCUMENTS

| | | | |
|---|---|---|---|
| 7,760,426 B2 * | 7/2010 | Hege, Jr. ................ | G02B 21/24 |
| | | | 359/368 |
| 9,438,773 B2 | 9/2016 | Howes | |
| 2004/0091259 A1 | 5/2004 | Hanzawa | |
| 2005/0276593 A1 * | 12/2005 | Yamasaki .............. | G03B 13/32 |
| | | | 396/114 |
| 2009/0167933 A1 | 7/2009 | Mura et al. | |
| 2013/0100271 A1 | 4/2013 | Howes | |

FOREIGN PATENT DOCUMENTS

| | | |
|---|---|---|
| CN | 204188876 U | 3/2015 |
| CN | 105264435 A | 1/2016 |
| CN | 205507214 U | 8/2016 |
| CN | 106940472 A | 7/2017 |
| CN | 206618896 U | 11/2017 |
| CN | 107807442 A | 3/2018 |
| JP | H06222283 A | 8/1994 |
| JP | 2004109554 A | 4/2004 |
| JP | 2009157054 A | 7/2009 |

OTHER PUBLICATIONS

WIPO, State Intellectual Property Office of the P.R. China, International Search Authority, International Search Report and Written Opinion mailed Jun. 15, 2018 in International Patent Application No. PCT/2018/079406, 9 pages.

* cited by examiner

OPTICAL ADAPTER FOR MICROSCOPE AND METHOD FOR ADJUSTING DIRECTION OF OPTICAL IMAGE

RELATED APPLICATION

This application is a continuation of U.S. patent application Ser. No. 16/496,045, which was filed on Sep. 20, 2019, which in turns claims the priority from International Application No. PCT/CN2018/079406 filed on 19 Mar. 2018 and claims priority from CN Application No. 201710168851.0 filed on Mar. 21, 2017; and CN Application No. 201710238871.0 filed on Apr. 13, 2017, which are hereby expressly incorporated by reference in their entirety for all purposes.

FIELD OF THE INVENTION

The present invention generally relates to medical devices and equipment, but not by way of limitation, to optical adapters for microscopes.

BACKGROUND OF THE DISCLOSURE

As shown in FIGS. 1A, 1B, and 1C, a conventional optical adapter B is used for connecting a beam splitter A from a microscope D to a digital camera equipment C1/C2/C3. The optical adapter B is configured to be rotatable around an axis of rotation so that it may be positioned in different rotational positions, usually 90 degrees between each position, thereby adjusting the direction of digital camera equipment C1, C2, and C3 in upward, forward, downward, or backward positions. This is performed by selecting the direction of the mount when connected to the beam splitter A, and by changing the angle required for reassembling.

An example of the conventional optical adapter B and its optical path is shown schematically in FIGS. 2A, 2B, and 2C. As it can be seen from these figures, the lens 3 and the right angle prism 41 (plane mirror is also acceptable) are sequentially arranged in the optical adapter B. When the optical adapter B is rotated to a different position, the reflective surface of the right angle prism 41 rotates about the optical axis. As such, the normal of the splitting surface of the beam splitter A and the normal of the reflective surface of the right angle prism 41 no longer remain parallel, thereby, the direction of the optical image will be rotated. For example, if the optical adapter B is in its initial position, i.e., the right angle lens does not rotate, and thus, the resulting optical image is as shown in FIG. 2A. When the optical adapter B rotates to the next gear, the reflective surface of the right angle prism 41 will rotate by 90 degrees, and the resulting optical image is as shown in FIG. 2B. Alternatively, the reflective surface of the right angle prism 41 rotates by 180 degrees when the optical adapter B further rotates to the next gear, and the resulting optical image is as shown in FIG. 2C.

Since the photosensitive unit of digital camera equipment is rectangular, and the output signals from the digital camera are sequentially set, there is going to be different image directions including: up, down, left and right. Consequently, images captured by the digital camera equipment need to be uploaded to a computer or a network for viewing, saving, editing and the like. Therefore, images with a wrong direction are not convenient for use and they need to be adjusted by a video software (with only 90 degrees multiple rotations), as shown in FIGS. 1A, 1B, and 1C. Therefore, there is a constant need to re-adjust the installation direction of digital camera equipment so as to rotate the photosensitive unit in an appropriate orientation, to ensure that the images captured by the photosensitive unit are in accordance with the direction of images observed in the microscope. Even so, there may still exist some inconsistency between the image displayed on the display of the digital camera equipment and the normal viewing direction of the operator, resulting in great inconvenience of use, e.g., FIG. 1D.

Moreover, the digital camera C used in the mobile phones or the tablet devices captures images by focusing on the beam splitter A of the microscope or uses a dedicated adapter in the camera (FIGS. 1A-1D). This may cause the captured images to be cut or not being able to fill the entire field of view of the digital camera due to existence of a mismatch between the angle of view and the pupil. Consequently, a user may have to manually zoom-in on the mobile phone or the tablet device to enlarge the image, which results in loss of information and image quality and further complex operations.

SUMMARY OF THE INVENTION

The present invention is proposed in view of the above aforementioned problems. In order to achieve the above purpose, the technical solution adopted in the present invention comprises: an optical adapter for connecting between a beam splitter of a surgical microscope or an ophthalmic slit lamp microscope and a digital camera equipment. Examples of the digital camera equipment may include mobile phones, tablet computers, cameras and video cameras with image capturing function. The optical adapter according to a first embodiment of the present invention includes a lens group located on an optical path and an optical image rotating unit for adjusting the direction of the optical image projected on a photosensitive unit of the digital camera equipment. The optical image rotating unit may include an optical image rotating lens group comprising a Dove roof prism, a Pechan prism, a Pechan roof prism or a Right angle prism located on the optical path. In this embodiment, the optical image rotating lens group is configured to be rotatable around optical axis independently with respect to the beam splitter. The optical adapter comprises a body housing, the body housing comprises a first body housing for connecting to the beam splitter and a second body housing for connecting to the digital camera equipment, the second body housing can perform a 360-degree stepless rotation relative to the first body housing, allowing a stepless adjustment of positioning of the digital camera equipment.

In another embodiment, the lens group may include at least a first lens unit for converging an outgoing light of the beam splitter into a real image, and a second lens unit for projecting the real image on the photosensitive unit of the digital camera equipment, the second lens unit being disposed at one end of the lens group. In this embodiment, an exit pupil of said lens group is located behind the second lens unit, and a distance between the exit pupil and an apex located on the rear optical surface of a final lens in said second lens unit is not more than 30 mm. Preferably, the first lens unit and the second lens unit are convex lens unit, and a focal length of the first lens unit is greater than a focal length of the second lens unit while a ratio of focal length between the first lens unit and the second lens unit is greater than 3.

In a preferred embodiment, the optical image rotating unit is disposed within the body housing such that the optical image rotating lens group and the lens group are both disposed in the body housing. In this way, all the optical elements are located within the body housing.

In this preferred embodiment, a rotating part is disposed on the body housing for rotating the optical image rotating lens group, the optical image rotating lens group is connected to the rotating part, the rotation of the optical image rotating lens group can be facilitated by the provision of the rotating part on the body housing, the rotating part may be a rotating joint on the body housing or the like.

In an alternative embodiment, a scale for indicating a rotational angle of the rotating part may be provided on the body housing and/or on the rotating part. In this way, the optical image rotating lens group can operate accurately using the scale, so that the rotation of optical image rotating lens group in the right direction can be easily facilitated.

In yet another embodiment, the optical rotating unit is connected to an outside of the body housing. In this embodiment, the optical rotating unit is connected to an outside of the body housing as a relatively independent component, and can be connected with the body housing fixedly or detachably. In this embodiment, except for the optical image rotating lens group, the lens group and/or other optical elements are still disposed within the body housing.

In yet another embodiment, the optical image rotating unit may be connected to one end of the body housing. For example, when the optical adapter is connected to the beam splitter the optical image rotating unit is adapted to be disposed between the beam splitter and the one end of the body housing. Or alternatively, the optical image rotating unit may be connected to the other end of the body housing. In this case, when the optical adapter is connected to the digital camera equipment, the optical image rotating unit is adapted to be disposed between the other end of the body housing and the digital camera equipment. In this way, the optical image rotating unit operates in two connection modes by being able to connect to both ends of the body housing.

In yet another embodiment, the optical adapter further includes a group of mirrors located on the optical path, where the group of mirrors can be disposed within the body housing. This group of mirrors may include at least one reflecting element having at least one of the reflector, pentaprism, right angle prism and right angle roof prism.

In yet another embodiment, the group of mirrors may include at least two reflecting elements that reflect the optical images at least two times. In this way, the direction of optical image on the photosensitive unit can be adjusted in two dimensions. Similarly, the number of reflecting elements may be increased sequentially to achieve multidimensional adjustment of the optical image.

In a preferred embodiment, the optical adapter may further include the digital camera equipment. In this embodiment, the digital camera equipment becomes an integral part of the optical adapter.

In accordance with a second aspect of the present invention, there is provided an optical adapter for connecting between a beam splitter of a surgical microscope or an ophthalmic slit lamp microscope and a digital camera equipment. The optical adapter according to the second aspect of the present invention may include a lens group located on an optical path and an optical image rotating lens group for adjusting the direction of optical image projected on the photosensitive unit of the digital camera equipment. In this embodiment, the optical image rotating lens group comprising a Dove roof prism, a Pechan prism, a Pechan roof prism or a Right angle prism is configured to be fixed on the optical path. The microscope optical adapter comprises a body housing, the body housing comprises a first body housing for connecting to the beam splitter and a second body housing for connecting to the digital camera equipment, the second body housing can perform a 360 degree stepless rotation relative to the first body housing, allowing a stepless adjustment of positioning of the digital camera equipment In accordance with a third aspect of the present invention, there is provided a process for adjusting a direction of an optical image using a microscope optical adapter in a microscope, the method includes the steps of: connecting the microscope optical adapter with a beam splitter of the microscope on its light incident end; connecting a digital camera equipment to the light emitting end of said microscope optical adapter; forming an optical image on a photosensitive unit of the digital camera equipment. The microscope optical adapter includes an optical image rotating unit for adjusting a direction of an optical image on a photosensitive unit of the digital camera equipment. The optical image rotating unit may include an optical image rotating lens group comprising a Dove roof prism, a Pechan prism, a Pechan roof prism or a Right angle prism which is configured to be rotatable around optical axis independently with respect to the beam splitter. When a light emitting direction of the microscopic optical adapter is changed by rotation of the optical image rotating unit, the optical image formed by the light emitted from different emission directions on the photosensitive unit of the digital camera equipment can be aligned with the image observed by the microscope without an adjustment of computer software. The microscope optical adapter comprises a body housing, the body housing comprises a first body housing for connecting to the beam splitter and a second body housing for connecting to the digital camera equipment, the second body housing can perform a 360-degree stepless rotation relative to the first body housing, allowing a stepless adjustment of positioning of the digital camera equipment By way of comparison with prior art, embodiments of the present invention provides the following advantages and effects as a result of the application of the above technical solutions.

Embodiments of the present invention provide for a system and method for real-time adjustment of the direction of an optical image on the photosensitive unit of a digital camera equipment, where regardless of the position of the digital camera a satisfactory direction of the optical image can be obtained with a simple user friendly and convenient structure.

BRIEF DESCRIPTION OF THE DRAWING

The present disclosure is described in conjunction with the appended figures.

In the appended figures, similar components and/or features may have the same reference label. Further, various components of the same type may be distinguished by following the reference label by a dash and a second label that distinguishes among the similar components. If only the first reference label is used in the specification, the description is applicable to any one the similar components having the same first reference label irrespective of the second reference label. For ease of understanding, the main components are listed below with their corresponding reference labels: 1: beam splitter prism; 20: Dove prism; 21: Dove roof prism; 22: Pechan prism; 23: Pechan roof prism; 3, 30, 31: lens group; 310: rear optical surface; 40: pentaprism; 41: right angle prism; 42: right angle roof prism; 5: body housing; 50: first body housing; 51: second body housing; 52: rotating part; A: beam splitter; B: optical adapter; C: digital camera; C1: tablet computer; C2: mobile phone; C3: camera; D: microscope; E: real image; F: apex; G: exit pupil.

DETAILED DESCRIPTION OF THE INVENTION

The present invention will be further described below with reference to the accompanying drawings and embodiments. As will be described further below, the optical image rotating lens group, as set forth in the embodiments I-IV, may include Dove prism or Dove roof prism which rotate around the optical axis to adjust the orientation of optical images captured by the digital camera. In order to avoid image mirroring caused by odd number of total reflections, a combination of prisms may be used in the following manners.

Embodiment I

Figure 1A:
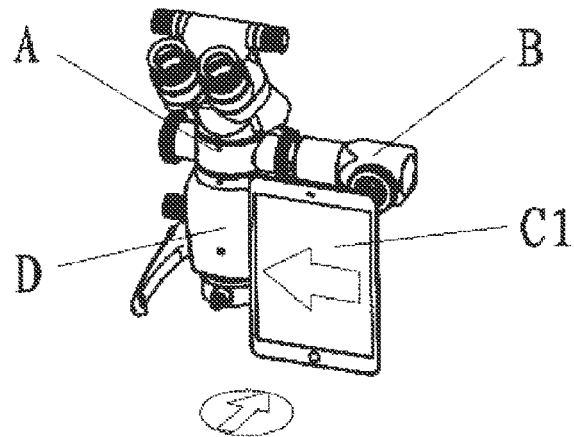
FIGS. 1A, 1B, 1C, and 1D illustrate an exemplary schematic diagram of a prior art optical adapter and a microscope.
Figure 1B:
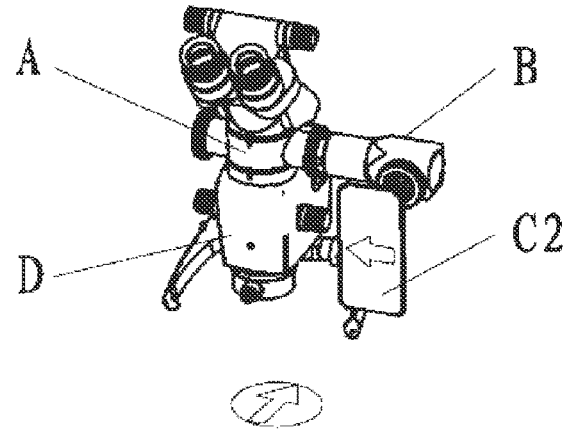
Figure 1C:
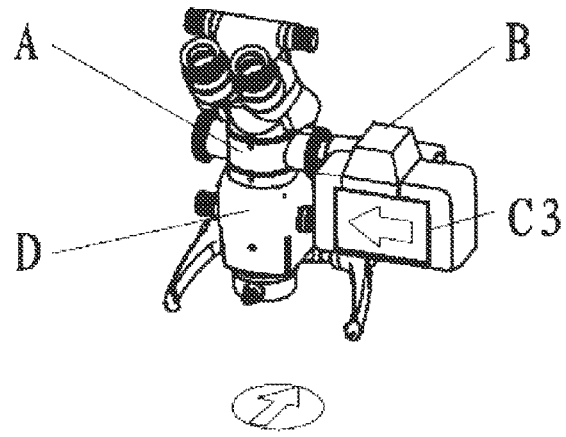
Figure 1D:
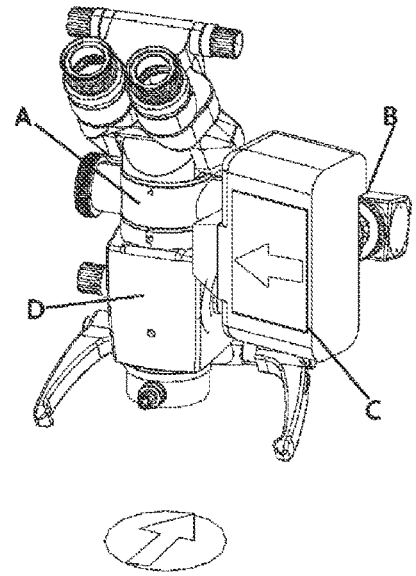
Figure 2A:
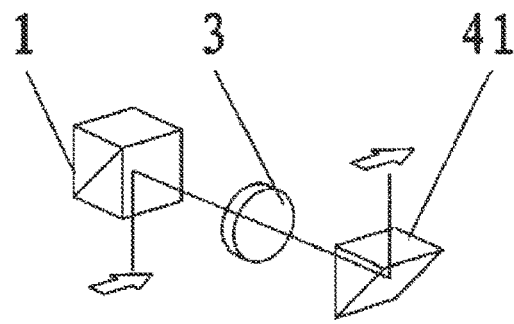
FIGS. 2A, 2B, and 2C illustrate an exemplary schematic diagram of an optical path of optical elements existing in the prior art optical adapters.
Figure 2B:
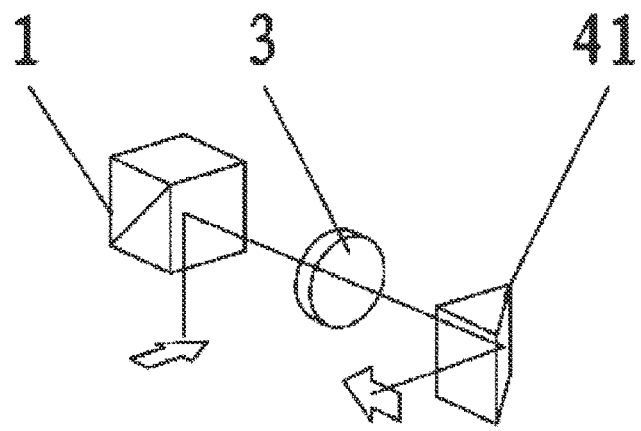
Figure 2C:
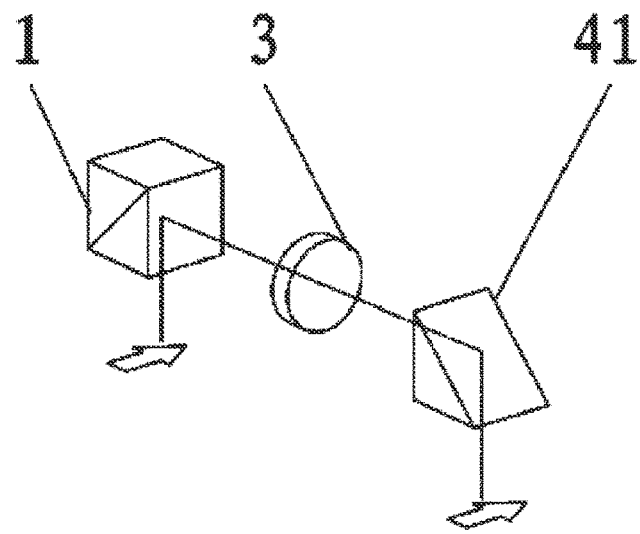
Figure 3:
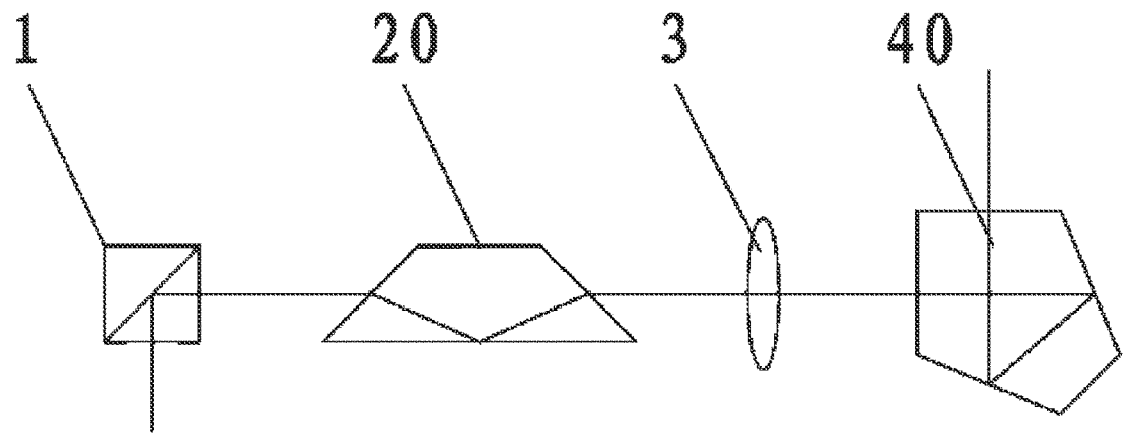
FIG. 3 illustrates a schematic diagram of an optical path of an optical adapter according to a first embodiment of the present invention.

Referring first to FIG. 3, an optical path of an optical adapter for a microscope according to the first embodiment of the present invention is shown. The optical adapter may include a Dove prism 20, a lens group 3 and a pentaprism 40 which are sequentially arranged on one splitting optical path of the beam splitter prism 1. As it can be seen form FIG. 3, the incident light is reflecting once inside the Dove prism 20 and twice inside the pentaprism 40 to ensure a total number of four times reflections. In this embodiment, the orientation of optical images formed on the photosensitive unit of the digital camera equipment C1, C2, and C3 can be adjusted by only rotating the Dove prism 20. This combination of prisms allows for avoiding a higher cost and more complicated process that are used in manufacturing of roof prisms.

Embodiment II

Figure 4:
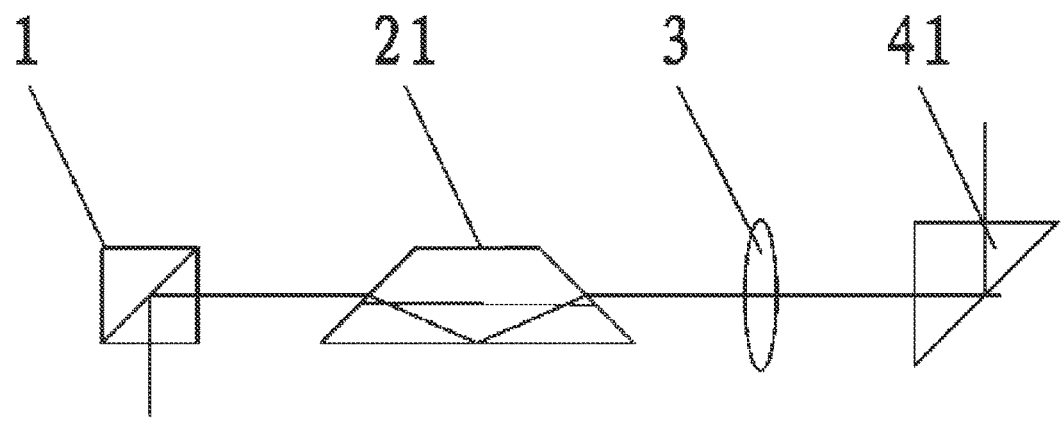
FIG. 4 illustrates a schematic diagram of an optical path of an optical adapter according to a second embodiment of the present invention.

Referring next to FIG. 4, an optical path of an optical adapter for a microscope according to the second embodiment of the present invention is shown. In this embodiment, the optical adapter includes a Dove roof prism 21, the lens group 3 and a right angle prism 41 which are sequentially arranged on the splitting optical path of the beam splitter prism 1. In this embodiment, the incident light is reflecting twice inside the Dove roof prism 21 and once inside the right angle prism 41 to ensure a total number of even reflections (four times). Similar to the first embodiment, the rotation of Dove roof prism 21 alone can adjust the orientation of the optical images formed on the photosensitive unit of the digital camera equipment C1, C2, and C3.

Embodiment III

Figure 5:
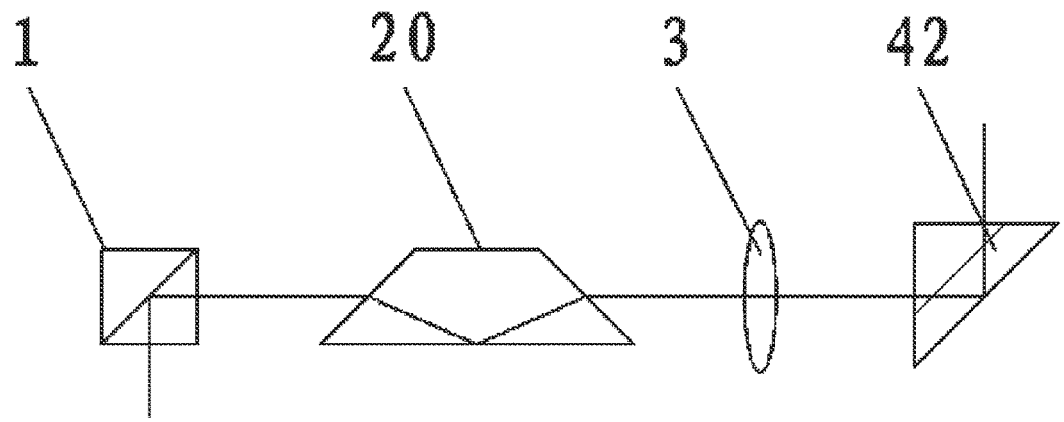
FIG. 5 illustrates a schematic diagram of an optical path of an optical adapter according to a third embodiment of the present invention.

With reference to FIG. 5, an optical path of an optical adapter for a microscope according to the third embodiment of the present invention is shown. In this embodiment, the optical adapter includes a Dove prism 20, the lens group 3 and a right angle roof prism 42 which are sequentially arranged on the splitting optical path of the beam splitter prism 1. In this embodiment, the incident light is reflecting once inside the Dove prism 20 and twice inside the right angle roof prism 42 to ensure a total number of even reflections (four times). Similar to the first embodiment, the rotation of Dove roof prism 20 alone can adjust the orientation of the optical images formed on the photosensitive unit of the digital camera equipment C1, C2, and C3.

Embodiment IV

Figure 6:
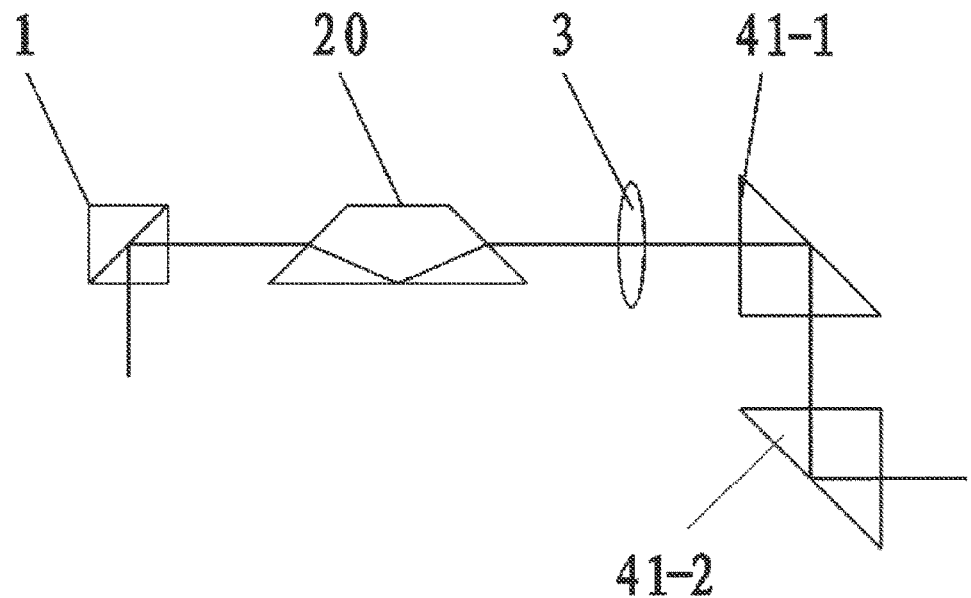
FIG. 6 illustrates a schematic diagram of an optical path of an optical adapter according to a fourth embodiment of the present invention.

FIG. 6 illustrates an optical path of an optical adapter for a microscope according to the fourth embodiment of the present invention. The fourth embodiment is different from the first embodiment in that the pentaprism 40 is replaced by two right angle prisms 41 (reference labels 41-1 & 41-2 in FIG. 6). In this embodiment, the incident light is reflecting once inside the Dove prism 20 and once inside each of the right angle prisms 41 to ensure a total number of even reflections (four times). This configuration also allows for avoiding a higher cost and more complicated process that are used in manufacturing of roof prisms. Similar to the previous embodiments, the optical elements of the fourth embodiment are sequentially arranged on the splitting optical path of the beam splitter prism 1. Using two right angle prisms 41 (reference labels 41-1 & 41-2 in FIG. 6) allows for two-dimensional adjustment of the optical image. Similarly, a multidimensional adjustment of the optical image can be achieved by adding more reflections. Here again the rotation of Dove prism 20 alone can adjust the orientation of the optical images formed on the photosensitive unit of the digital camera equipment C1, C2, and C3.

The optical image rotating lens group, as set forth in the embodiments V-VIII, may include Pechan prism or Pechan roof prism which rotate around the optical axis to adjust the orientation of optical images captured by the digital camera. The optical path of optical elements in the embodiments V-VIII is different from the previous embodiments I-IV, in that the lens group 3 is located as the first optical element of the optical path. In order to avoid image mirroring caused by odd number of total reflections, a combination of prisms may be used in the following manners.

Embodiment V

Figure 7:
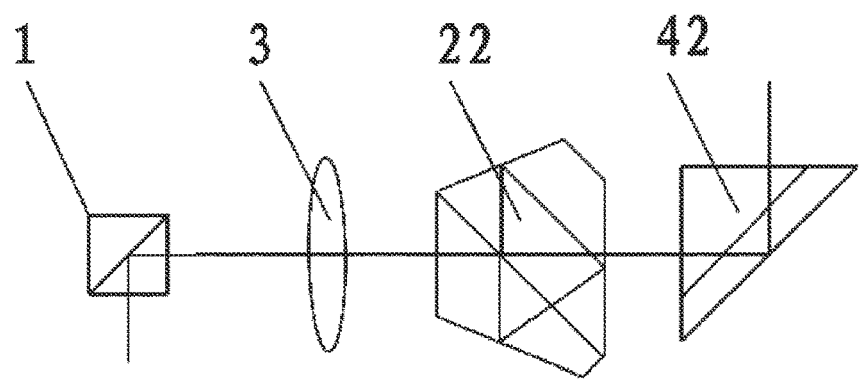
FIG. 7 illustrates a schematic diagram of an optical path of an optical adapter according to a fifth embodiment of the present invention.

Referring next to FIG. 7, an optical path of an optical adapter for a microscope according to the fifth embodiment of the present invention is shown. The optical adapter may include the lens group 3, a Pechan prism 22 and a right angle roof prism 42 which are sequentially arranged on the splitting optical path of the beam splitter prism 1. As it can be seen form FIG. 7, the incident light is reflecting five times inside the Pechan prism 22 and twice inside the right angle roof prism 42 to ensure a total number of eight times reflections. Here again, the orientation of optical images formed on the photosensitive unit of the digital camera equipment C1, C2, and C3 can be adjusted by only rotating the Pechan prism 22.

Embodiment VI

Figure 8:
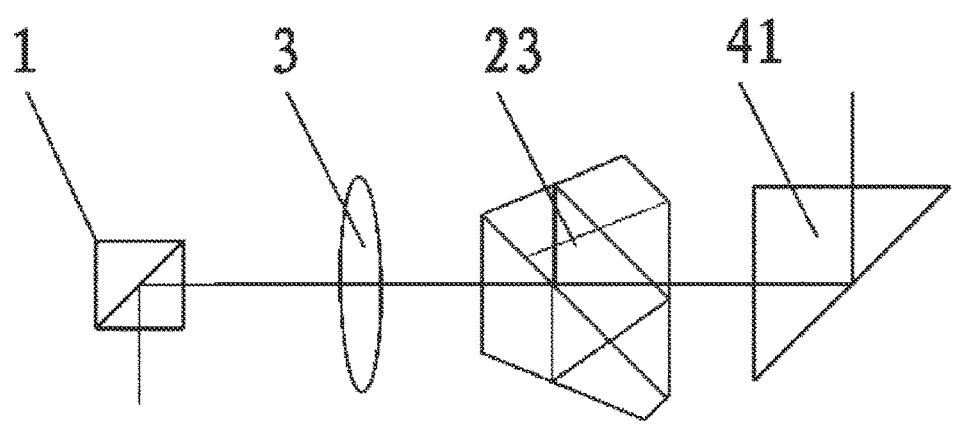
FIG. 8 illustrates a schematic diagram of an optical path of an optical adapter according to a sixth embodiment of the present invention.

FIG. 8 illustrates an optical path of an optical adapter for a microscope according to the sixth embodiment of the present invention. In this embodiment, the optical adapter may include the lens group 3, a Pechan roof prism 23 and a right angle prism 41. Similar to the fifth embodiment, the optical elements are sequentially arranged on the splitting optical path of the beam splitter prism 1 with the lens group 3 being disposed as the first optical element of the optical path. In this embodiment, the incident light is reflecting six times inside the Pechan roof prism 23 and once inside the right angle prism 41 to ensure a total number of even reflections (eight times). Here again, the rotation of Pechan roof prism 23 alone can adjust the orientation of the optical images formed on the photographic unit of the digital camera equipment C1, C2, and C3.

Embodiment VII

Figure 9:
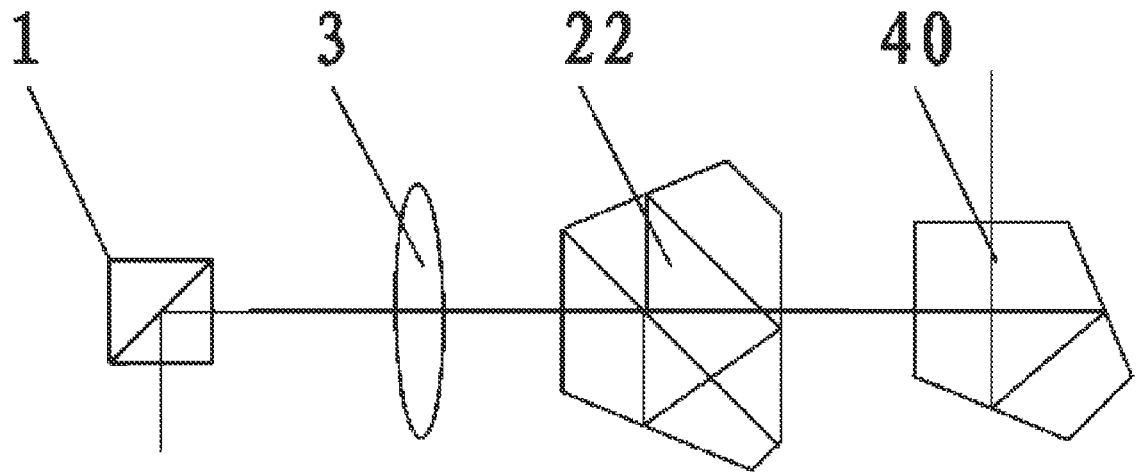
FIG. 9 illustrates a schematic diagram of an optical path of an optical adapter according to a seventh embodiment of the present invention.

With reference to FIG. 9, an optical path of an optical adapter for a microscope according to the seventh embodiment of the present invention is shown. In this embodiment, the optical adapter may include the lens group 3, a Pechan prism 22 and a pentaprism prism 40 which are sequentially arranged on the splitting optical path of the beam splitter prism 1 with the lens group 3 being disposed as the first optical element of the optical path. In this embodiment, the incident light is reflecting five times inside the Pechan prism 22 and twice inside the pentaprism 40 to ensure a total number of even reflections (eight times). This combination of prisms allows for avoiding a higher cost and more complicated process that are used in manufacturing of roof prisms. Similar to the previous embodiments, the rotation of Pechan prism 22 alone can adjust the orientation of the optical images formed on the photosensitive unit of the digital camera equipment C1, C2, and C3.

Embodiment VIII

Figure 10:
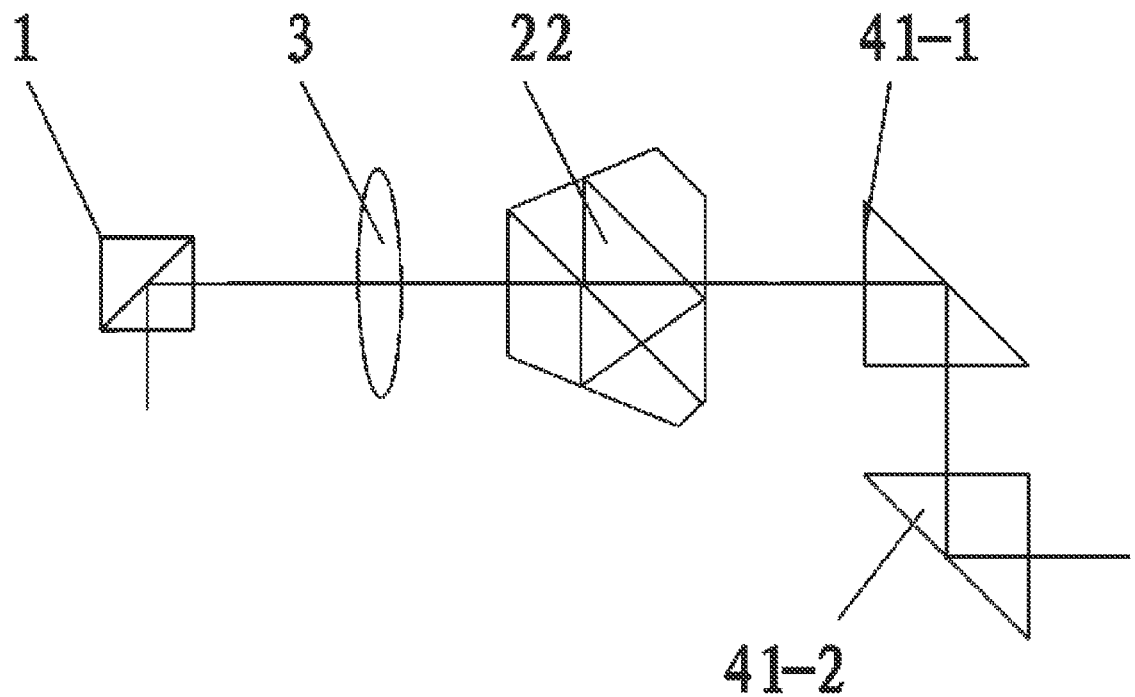
FIG. 10 illustrates a schematic diagram of an optical path of an optical adapter according to an eighth embodiment of the present invention.

FIG. 10 illustrates an optical path of an optical adapter for a microscope according to the eighth embodiment of the present invention. The eighth embodiment is different from the fifth embodiment in that the right angle roof prisms 42 is replaced by two right angle prisms 41 (reference labels 41-1 & 41-2 in FIG. 10). In this embodiment, the incident light is reflecting five times inside the Pechan prism 22 and once inside each of the right angle prisms 41 to ensure a total number of even reflections (eight times). Similar to the previous embodiment (7th embodiment), this configuration also allows for avoiding a higher cost and more complicated process that are used in manufacturing of roof prisms. Here again, the optical elements of the eighth embodiment are sequentially arranged on the splitting optical path of the beam splitter prism 1 with the lens group 3 being disposed as the first optical element of the optical path. Using two right angle prisms 41 (reference labels 41-1 & 41-2 in FIG. 10) allows for two-dimensional adjustment of the optical image. Similarly, a multidimensional adjustment of the optical image can be achieved by adding more reflections. Here again the rotation of Pechan prism 22 alone can adjust the orientation of the optical images formed on the photosensitive unit of the digital camera equipment C1, C2, and C3.

Embodiment IX

Figure 11:
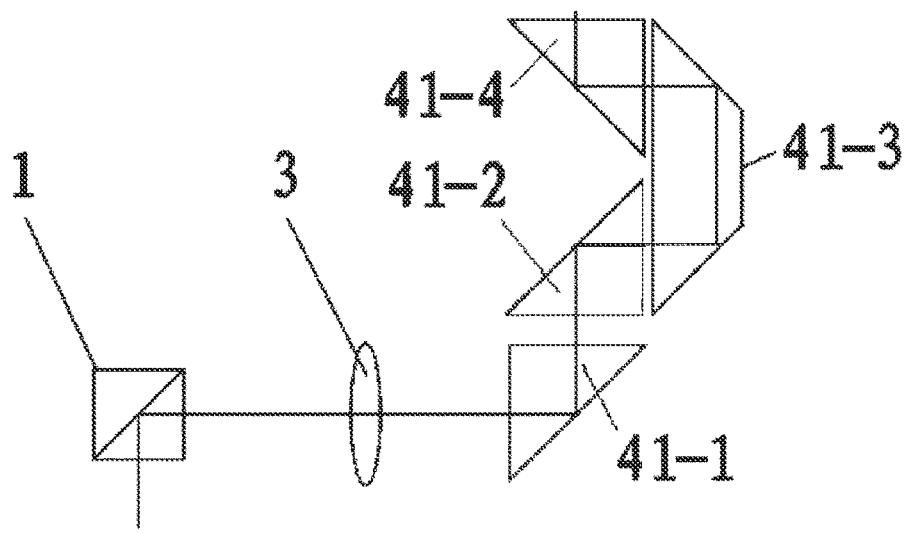
FIG. 11 illustrates a schematic diagram of are optical path of an optical adapter according to a ninth embodiment of the present invention.

Referring next to FIG. 11, an exemplary optical path of an optical adapter for a microscope according to the ninth embodiment of the present invention is shown. In this embodiment, the optical adapter may include the lens group 3 and a group of mirrors which are sequentially arranged on the splitting optical path of the beam splitter prism 1 with the lens group 3 being disposed as the first optical element of the optical path. As can be seen from FIG. 11, the group of mirrors includes four right angle prisms 41 (reference labels 41-1, 41-2, 41-3 & 41-4) where the optical image rotating lens group contains three right angle prisms 41 (reference labels 41-2, 41-3, & 41-4 in FIG. 11) at the end of the optical path. In this embodiment, the right angle prism 41-4 can follow the rotation of digital camera equipment while the relative rotational angle between the right angle prism 41-4 and the right angle prism 41-3 remains always the same as the relative rotational angle between the right angle prism 41-2 and the right angle prism 41-3. This is achieved by a mechanical linkage which allows for continuously adjusting the orientation of digital camera equipment C1, C2, and C3 so as to automatically maintain the direction of optical images constant.

Embodiment X

Figure 12:
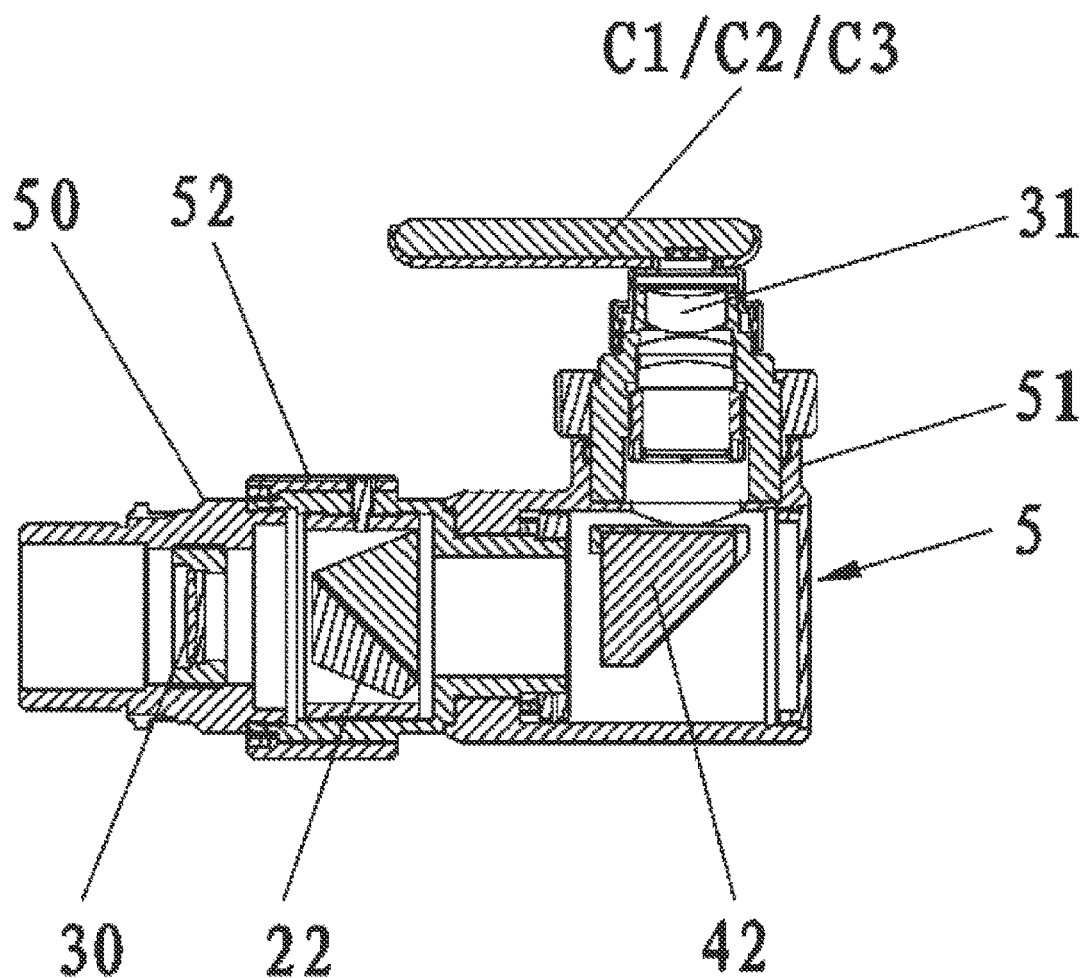
FIG. 12 illustrates a cross-sectional view of an exemplary embodiment of an optical adapter for a microscope according to a tenth embodiment of the present invention.

FIG. 12 illustrates a cross-sectional view of an exemplary embodiment of an optical adapter for a microscope according to the tenth embodiment of the present invention. As shown in this figure, the optical adapter may include an L-shaped body housing 5, where one end of the body housing 5 is configured to connect to the beam splitter A, while the other end of the body housing 5 is configured to connect to the digital camera equipment C1, C2, and C3. In this embodiment, the lens group may include a first lens unit 30 and a second lens unit 31. Inside the body housing 5, a first lens unit 30, a Pechan prism 22, a right angle roof prism 42, and a second lens unit 31 are sequentially arranged on the splitting optical path of the beam splitter prism from the beam splitter. Here again the rotation of the Pechan prism 22 alone can adjust the orientation of the optical images formed on the photosensitive unit of the digital camera equipment C1, C2, and C3.

In this embodiment, the L-shaped body housing 5 further includes a first body housing 50 for connecting to the beam splitter A of the microscope and a second body housing 51 for connecting to the digital camera equipment C1, C2, and C3. The first body housing 50 is set vertically relative to the second body housing 51, and the second body housing 51 can perform a 360-degree stepless rotation relative to the first body housing 50, allowing a stepless adjustment of the positioning of the digital camera equipment C1, C2, and C3. The first body housing 50 and/or the second body housing 51 is provided with a scale for indicating the rotation angle of the second body housing 51.

In order to facilitate the rotation of the Pechan prism 22, the body housing 5 is further provided with a rotating part 52 which is disposed on a top surface of the first body housing 50. As shown in FIG. 12, the Pechan prism 22 is connected with the rotating part 52 such that the rotation of the Pechan prism 22 about the optical axis can be achieved by operating the rotating part 52. In addition, the body housing 5 and/or the rotating part 52 may be provided with another scale for indicating a rotation angle of the rotating part 52. This scale is configured to match the scale of the second body housing 51 such that the rotating part 52 can operate quickly and accurately so as to facilitate the rotation of the Pechan prism 22.

In an alternative embodiment, a lens group, an optical image rotating lens group and a group of mirrors may be additionally disposed within the body housing 5 of the optical adapter B. In this embodiment, according to different combinations of the lens group, the optical image rotating lens group and the group of mirrors, the optical image rotating lens group may be disposed between the beam splitter A and the body housing 5 of the optical adapter B, or between the body housing 5 of the optical adapter B and the digital camera equipment C1, C2, and C3.

Figure 13:
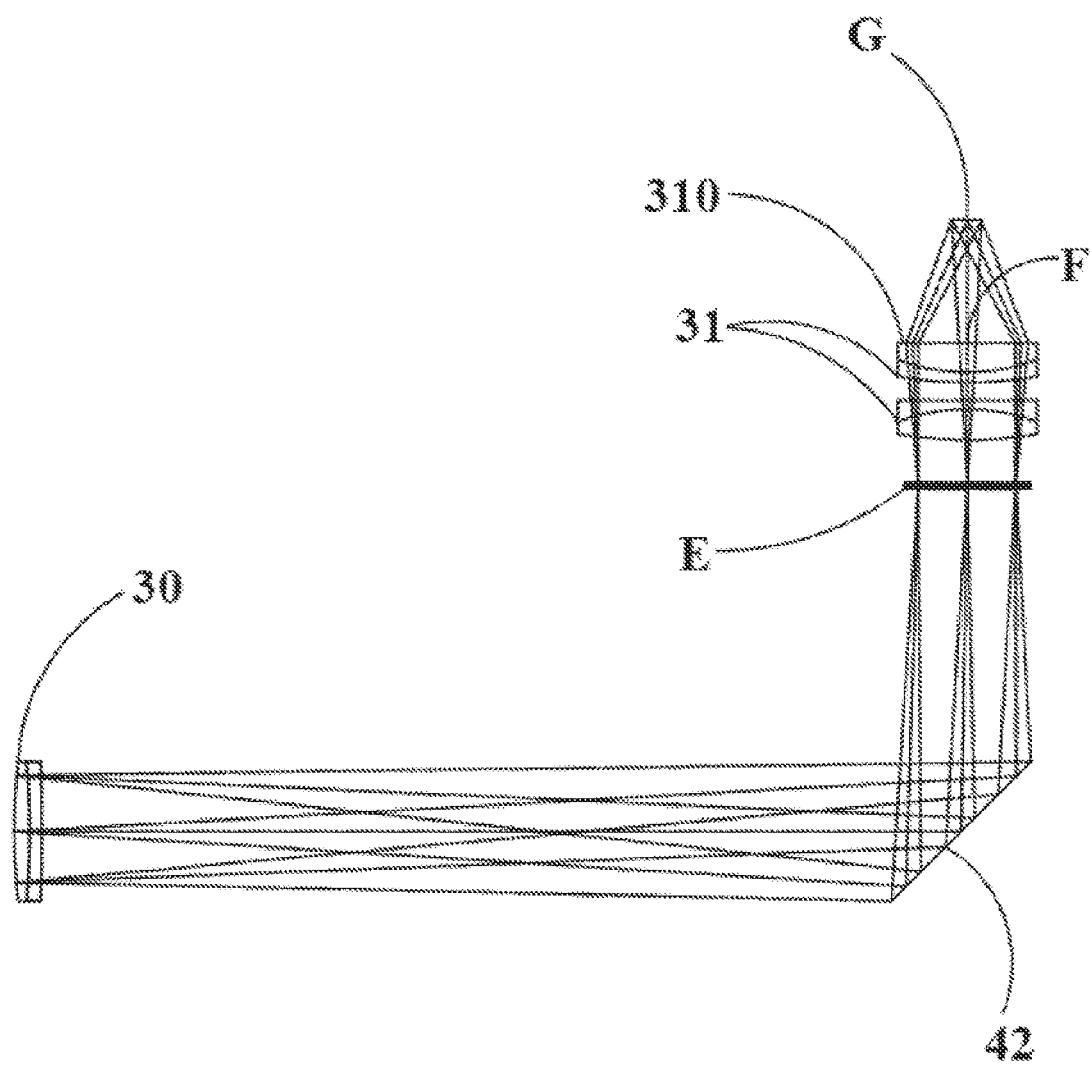
FIG. 13 illustrates a schematic diagram of an optical path of the optical adapter according to the tenth embodiment of the present invention.
Figure 14A:
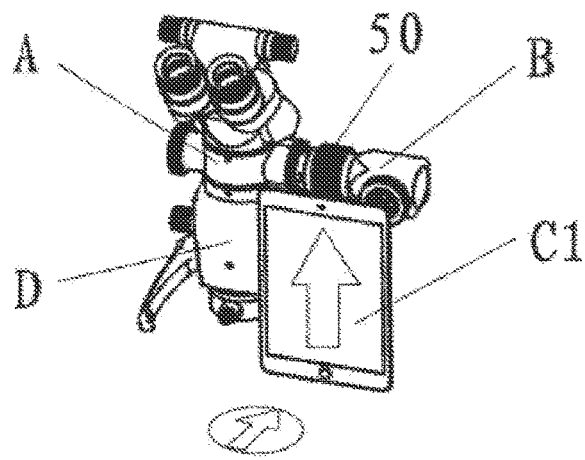
FIGS. 14A, 14B, and 14C illustrate an exemplary schematic diagram of an optical adapter according to the embodiments of the present invention and a microscope.
Figure 14B:
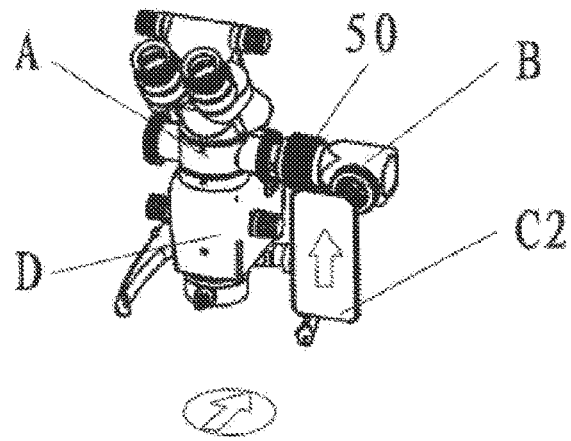
Figure 14C:
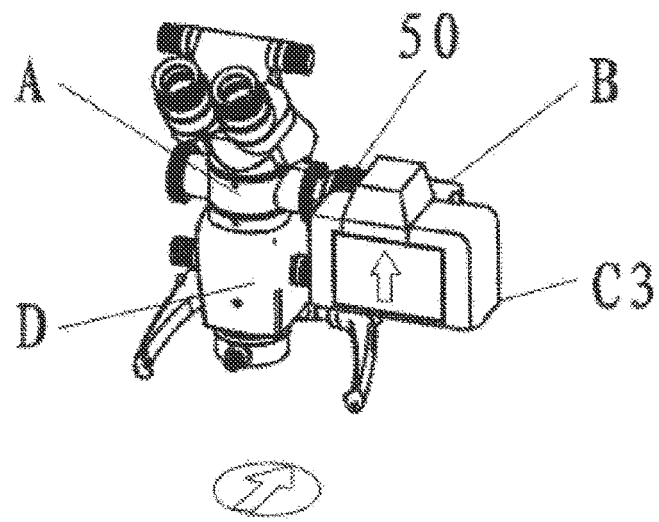

With reference to FIG. 13, an optical path of the optical adapter according to the tenth embodiment of the present invention is shown. As described further above, the lens group of the optical adapter of the present embodiment may include a first lens unit 30 and a second lens unit 31. The first lens unit 30 which is located as the first optical element of the optical path and is used for converging an outgoing light of the beam splitter A into a real image E. The second lens unit 31 which are located as the last element of the optical path at the other end of the optical adapter and is used for projecting the real image E on the photosensitive unit of the digital camera equipment C1/C2/C3. As shown in FIG. 13, an exit pupil G of the lens group is located behind the second lens unit 31, and a distance between the exit pupil G and an apex F located on a rear optical surface 310 of the last or final lens in the second lens unit 31 is not more than 30 mm.

More specifically, since the distance between an entrance pupil of a micro camera (the digital camera equipment C1/C2/C3) and the rear optical surface 310 from the last lens of the second lens unit 31 is generally less than 10 mm, the distance of the exit pupil G to the rear optical surface 310 of the present embodiment does not exceed more than 30 mm to ensure adjustability, and therefore, matching with the entrance pupil of the micro camera. The imaging range of the micro camera on a mobile phone is generally 45 degrees×60 degrees (rectangular light sensing unit), where after being amplified 8-10 times by the optical adapter described in the present embodiment, electronic zoom-in is no longer required, and the optical performance of the micro camera can be fully utilized.

In a preferred embodiment, the first lens unit 30 and the second lens unit 31 are convex lens units where a focal length of the first lens unit 30 is greater than a focal length of the second lens unit 31. More preferably, a ratio of focal length between the first lens unit 30 and the second lens unit 31 is greater than 3. Accordingly, a corresponding focusing mechanism may also be required to achieve the above-mentioned focal length adjustment between the first lens group 30 and the second lens group 31. In addition, each of the first lens unit 30 and the second lens unit 31 may further include one or more of an iris, a color filter and a polarizer. In this way, the size of the light aperture may be adjusted freely by setting the iris, the shape of the light may be kept approximately circular, and the stray light can be eliminated by the color filter and the polarizer.

By configuring the optical image rotating lens group as described in the above-mentioned embodiments, the direction of the optical image can be adjusted by independently rotating the optical image rotating lens group to ensure the most appropriate image observation in the microscope, regardless of positioning of the digital camera equipment C1, C2, C3, e.g., facing upward, downward, forward or backward. Please refer to the comparison between FIGS. 1A, 1B, 1C and FIGS. 14A, 14B, 14C.

The above embodiments are only for illustrating technical ideas and features of the present invention, and are intended to enable those skilled in the art to understand and implement the contents of the present invention, and are not intended to limit the scope of the protection of the present invention. Any equivalent changes or modifications made according to the spirit of the present invention shall be covered within the scope of the protection of the present invention.

What is claimed is:

1. An optical adapter for connecting between a beam splitter of a surgical microscope or an ophthalmic slit lamp microscope and a digital camera equipment, the optical adapter comprising:

a lens group located on an optical path; and an optical image rotating unit capable of adjusting a direction of an optical image on a photosensitive unit of the digital camera equipment, said optical image rotating unit comprises an optical image rotating lens group comprising a Dove roof prism, a Pechan prism, a Pechan roof prism or a Right angle prism located on the optical path, wherein said optical image rotating lens group is configured to be rotatable around optical axis independently with respect to the beam splitter;

wherein the optical adapter comprises a body housing, the body housing comprises a first body housing for connecting to the beam splitter and a second body housing for connecting to the digital camera equipment, the second body housing can perform a 360-degree stepless rotation relative to the first body housing, allowing a stepless adjustment of positioning of the digital camera equipment;

the lens group comprises at least a first lens unit for converging an outgoing light of the beam splitter into a real image, and a second lens unit for projecting said real image on the photosensitive unit of the digital camera equipment, said second lens unit being disposed at an opposite end of the optical path compared to said first lens unit, wherein an exit pupil of said lens group is located before the second lens unit, and a distance between said exit pupil and an apex located on a rear optical surface of a last lens in said second lens unit is not more than 30 mm;

wherein the first lens unit and the second lens unit are convex lens unit, and a focal length of said first lens unit is greater than a focal length of said second lens unit; and wherein a ratio of focal length between the first lens unit and the second lens unit is greater than 3.

2. The optical adapter of claim 1, wherein a rotating part is disposed on the body housing for rotating the optical image rotating lens group, said optical image rotating lens group being connected to said rotating part.

3. The optical adapter of claim 2, wherein a scale for indicating a rotational angle of the rotating part is provided on the body housing and/or on the rotating part.

4. The optical adapter of claim 1, wherein the optical image rotating unit being connected to an outside of the body housing.

5. The optical adapter of claim 4, wherein when the optical adapter is connected to the beam splitter, the optical image rotating unit is adapted to be disposed between the beam splitter and the one end of the body housing.

6. The optical adapter of claim 4, wherein when the optical adapter is connected to the digital camera equipment, the optical image rotating unit is adapted to be disposed between the digital camera equipment and at said another end of the body housing.

7. The optical adapter of claim 1, wherein the optical adapter further comprises a group of mirrors located on the optical path, said group of mirrors including at least one reflecting element which comprises a mirror, a pentaprism, a right angle prism and a right angle roof prism.

8. The optical adapter of claim 7, wherein the group of mirrors are selected from the group consisting of a Right Angle Roof Prism, a Pentaprism, an even number of Right Angle Prisms when the optical image rotating lens group comprises a Dove Prism or a Pechan prism, and an odd number of Right Angle Prisms when the optical image rotating lens group comprises a Dove Roof Prism or a Pechan Roof prism.

9. The optical adapter of claim 7, wherein the group of mirrors comprising at least three Right Angle Prisms when optical image rotating lens group comprises a Right Angle Prism.

10. A microscope optical adapter for connecting between a beam splitter of a microscope and a digital camera equipment, the microscope optical adapter comprising:

a lens group located on an optical path; and an optical image rotating unit for adjusting a direction of an optical image on a photosensitive unit of the digital camera equipment, said optical image rotating unit comprises an optical image rotating lens group comprising a Dove roof prism, a Pechan prism, a Pechan roof prism or a Right angle prism which is configured to be fixed on an optical path, the microscope optical adapter comprises a body housing, the body housing comprises a first body housing for connecting to the beam splitter and a second body housing for connecting to the digital camera equipment, the second body housing can perform a 360-degree stepless rotation relative to the first body housing, allowing a stepless adjustment of positioning of the digital camera equipment, the lens group comprises at least a first lens unit for converging an outgoing light of the beam splitter into a real image, and a second lens unit for projecting said real image on the photosensitive unit of the digital camera equipment, said second lens unit being disposed at an opposite end of the optical path compared to said first lens unit, wherein an exit pupil of said lens group is located before the second lens unit, and a distance between said exit pupil and an apex located on a rear optical surface of a last lens in said second lens unit is not more than 30 mm.

11. The microscope optical adapter of claim 10, wherein the microscope comprises a surgical microscope or an ophthalmic slit lamp microscope and the digital camera equipment comprises mobile phones, tablet computers, cameras, video cameras with image capturing function.

12. A method for adjusting a direction of an optical image using a microscope optical adapter in a microscope, the method comprising the steps of:

connecting the microscope optical adapter with a beam splitter of the microscope on its light incident end;

connecting a digital camera equipment to the light emitting end of said microscope optical adapter;

forming an optical image on a photosensitive unit of the digital camera equipment, wherein:

the microscope optical adapter comprises a lens group located on an optical path, and an optical image rotating unit for adjusting a direction of an optical image on a photosensitive unit of the digital camera equipment, the optical image rotating unit comprises an optical image rotating lens group comprising a Dove roof prism, a Pechan prism, a Pechan roof prism or a Right angle prism configured to be rotatable around optical axis independently with respect to the beam splitter, when a light emitting direction of the microscopic optical adapter is changed by rotation of the optical image rotating unit, the optical image formed by the light emitted from different emission directions on the photosensitive unit of said digital camera equipment can be aligned with the image observed by said microscope without an adjustment of computer software, the microscope optical adapter comprises a body housing, the body housing comprises a first body housing for connecting to the beam splitter and a second body housing for connecting to the digital camera equipment, the second body housing can perform a 360-degree stepless rotation relative to the first body housing, allowing a stepless adjustment of positioning of the digital camera equipment, the lens group comprises at least a first lens unit for converging an outgoing light of the beam splitter into a real image, and a second lens unit for projecting said real image on the photosensitive unit of the digital camera equipment, said second lens unit being disposed at an opposite end of the optical path compared to said first lens unit, wherein an exit pupil of said lens group is located before the second lens unit, and a distance between said exit pupil and an apex located on a rear optical surface of a last lens in said second lens unit is not more than 30 mm.

13. The method of claim 12, wherein the image forming step comprises a step of passing light from the beam splitter of the microscope respectively through the optical image rotating lens group and a group of mirrors located on the optical path to form the optical image on the photosensitive unit of the digital camera equipment.

14. The method of claim 12, wherein the microscope comprises a surgical microscope or an ophthalmic slit lamp microscope and the digital camera equipment comprises mobile phones, tablet computers, cameras, video cameras with image capturing function.

* * * * *